(12) United States Patent
Hanna et al.

(10) Patent No.: US 8,586,587 B2
(45) Date of Patent: Nov. 19, 2013

(54) CRYSTALLINE MOLECULAR COMPLEX OF TADALAFIL AND METHYLPARABEN

(75) Inventors: Mazen Hanna, Lutz, FL (US); Ning Shan, Tampa, FL (US); Miranda L. Cheney, Tampa, FL (US); David R. Weyna, Tampa, FL (US)

(73) Assignee: Thar Pharmaceuticals, Inc., Pittsburgh, PA (US)

( * ) Notice: Subject to any disclaimer, the term of this patent is extended or adjusted under 35 U.S.C. 154(b) by 0 days.

(21) Appl. No.: 13/203,297

(22) PCT Filed: Feb. 25, 2010

(86) PCT No.: PCT/US2010/025421
§ 371 (c)(1),
(2), (4) Date: Nov. 11, 2011

(87) PCT Pub. No.: WO2010/099323
PCT Pub. Date: Sep. 2, 2010

(65) Prior Publication Data
US 2012/0046297 A1    Feb. 23, 2012

Related U.S. Application Data

(60) Provisional application No. 61/208,624, filed on Feb. 26, 2009.

(51) Int. Cl.
*A61K 31/495*    (2006.01)
(52) U.S. Cl.
USPC .............................. 514/250; 544/343; 549/469

(58) Field of Classification Search
USPC .............................. 514/250; 544/343; 549/469
See application file for complete search history.

(56) References Cited

U.S. PATENT DOCUMENTS

| | | |
|---|---|---|
| 4,490,371 A | 12/1984 | Jones et al. |
| 5,859,006 A | 1/1999 | Daugan |
| 6,140,329 A | 10/2000 | Daugan |
| 6,821,975 B1 | 11/2004 | Anderson et al. |
| 6,943,166 B1 | 9/2005 | Pullman et al. |
| 7,182,958 B1 | 2/2007 | Oren et al. |
| 7,452,555 B2 | 11/2008 | Childs |
| 2003/0139429 A1 | 7/2003 | Cohen |
| 2003/0224006 A1 | 12/2003 | Zaworotko |
| 2006/0111571 A1 | 5/2006 | Wizel et al. |

OTHER PUBLICATIONS

European Extended Search Report of European Patent Application No. EP 10 74 6835 (related to PCT/US2010/025421), dated Jun. 26, 2012.
Shan et al., "The role of cocrystals in pharmaceutical science", Drug Discovery Today, vol. 13, Nos. 9/10, pp. 440-446, May 1, 2008.
Tampubolon et al., "Densitometric Determination of Tadalafil Citrate in Tablets: Validation of the Method", Journal of Liquid Chromatography & Related Technologies, vol. 29, No. 18, pp. 2753-2765, Jan. 1, 2006.

*Primary Examiner* — Douglas M Willis
(74) *Attorney, Agent, or Firm* — J.A. Lindeman & Co., PLLC (57) ABSTRACT

The invention relates to novel crystalline forms of tadalafil suitable for pharmaceutical compositions in drug delivery systems for humans. More particularly, the invention relates to crystalline molecular complexes of tadalafil and methylparaben.

9 Claims, 12 Drawing Sheets

CRYSTALLINE MOLECULAR COMPLEX OF TADALAFIL AND METHYLPARABEN

CROSS REFERENCE TO RELATED APPLICATIONS

This application claims priority to PCT International Application No. PCT/US2010/025421, filed Feb. 25, 2010, which claims priority to U.S. Provisional Application 61/208,624, filed Feb. 26, 2009, which is incorporated herein by reference.

TECHNICAL FIELD

The invention pertains to novel crystalline forms of the drug tadalafil, as well as methods for their preparation and use. One or more of these forms can be used as a solid dosage form in pharmaceutical compositions in a variety of drug delivery systems.

BACKGROUND OF THE INVENTION

Tadalafil is known as (6R-trans)-6-(1,3-benzodioxol-5-yl)-2,3,6,7,12,12a-hexahydro-2-methyl-pyrazino[1',2':1,6]pyrido[3,4-b]indole-1,4-dione, has the formula $C_{22}H_{19}N_3O_4$ representing a molecular weight of 389.41 g/mol and is depicted by the following chemical structure:

Tadalafil was originally developed by ICOS in 1994 and marketed via collaboration with Eli Lilly that subsequently took over ICOS in 2007. Tadalafil is a white solid particulate material that is practically insoluble in water. It is sparingly soluble in tetrahydrofuran and chloroform but is soluble in dioxane. Tadalafil has an apparent partition coefficient (log $P)_{app}$=1.7 in n-octanol/buffer pH 7.4.

Tadalafil, currently used for the treatment of erectile dysfunction (ED) under the Cialis® brand name, is a cGMP (cyclic gaunosine monophosphate) specific phosphodiesterase 5 (PDE5) inhibitor which enhances the effect of nitric oxide at the nerve ending and endothelial cells in the corpus cavernosum by inhibiting phosphodiesterase type 5 in the corpus cavernosum of the penis. This results in vasodilation, increased inflow of blood into the corpus cavernosum, and ensuing penile erection upon sexual stimulation. Tadalafil is also being investigated currently as a treatment for pulmonary hypertension. For ED treatment tadalafil is manufactured as a tablet for daily use (2.5 and 5 mg) with doses ranging from 5-20 mg as needed. See Cialis® Prescribing Information, February 2010. Tadalafil, the method of preparing tadalafil, its therapeutic uses, and pharmaceutical compositions containing it are described in U.S. Pat. Nos. 5,859,006; 6,140,329; 6,821,975; 6,943,166; and 7,182,958 which are incorporated herein by reference in their entirety.

A major limitation on its use to treat ED, which could be due in part to its very low aqueous solubility, is the fact that tadalafil takes from 0.5 to 6 hours (Tmax) to achieve the mean peak plasma concentration (Cmax) regardless of food intake. Therefore enhancing the aqueous solubility and subsequently the rate of dissolution can lead to a shortened Tmax and produce a quicker onset of action. In addition, this reduces the residence time in the GI tract and decreases the possibility of producing undesirable side effects through long contact with the GI membrane.

Different crystalline polymorphic forms of tadalafil have been disclosed in the literature (see for example U.S. Patent application 2006/0111571 A1). There are eight known polymorphs including forms II and III which are acetone and methylethyl ketone solvates, respectively.

In general, active pharmaceutical ingredients (APIs) in pharmaceutical compositions can be prepared in a variety of different chemical forms including chemical derivatives, solvates, hydrates, cocrystals and/or salts. Such compounds can also be prepared in different physical forms of the same chemical composition. For example, they may be amorphous, may have different crystalline forms (polymorphs), and/or may exist in different solvated or hydrated states with no change in the chemical composition of the original API. The discovery of new crystalline forms of a pharmaceutically useful compound may provide an opportunity to improve the physico-chemical characteristics and subsequently the clinical performance of such a compound. Additionally it expands the array of resources available for designing, for example, a pharmaceutical dosage form of an API with a targeted/sustained release profile or improved shelf life due to higher physical stability, improved particle size or size distribution, or powder flowability and handling for easier downstream processing or even for changing its route of delivery.

For example, crystalline forms of the same chemical composition (polymorphs) can have different aqueous solubilities from one another, where typically the more thermodynamically stable the polymorph the less soluble it becomes. In addition, polymorphs of an API can also differ in physico-chemical properties such as solid phase stability, higher shelf-life, bioavailability, particle morphology, vapor pressure, density, color, melting point and compressibility. However, it is sometimes difficult to produce the desired polymorph consistently or there is little improvement in their aqueous solubility or characterizing of all polymorphic forms can be challenging. In addition, if only one polymorph is discovered then there is less opportunity to manipulate and improve physico-chemical properties of the API. These limitations can adversely affect the API formulation into a usable dosage form or even force pharmaceutical companies to abandon the API's development.

Therefore it would be highly appreciable to generate novel crystalline molecular complexes, such as cocrystals, that can address such limitations and enhance the properties of an API such as aqueous solubility, rate of dissolution, bioavailability, Cmax, Tmax, solid phase stability, shelf life, downstream processability (e.g. flowability, compressibility, degree of brittleness, particle size and size distribution), crystallization of amorphous compounds, decrease polymorphic form diversity, reduce toxicity, taste masking, and/or its production and manufacturing methods efficiency. For oral delivery of solid dosage forms, it is frequently advantageous to have novel crystalline forms of drug materials that possess such improved properties and particularly increased aqueous solubility and solid phase stability. It is also desirable in general to increase the dissolution rate of such solid forms, increase bioavailability, and provide a more rapid onset to quicken the therapeutic effect. In addition, it is useful to have a crystal form which, when administered to a subject, reaches a peak plasma level faster and has a longer lasting therapeutic plasma concentration, when compared to other existing forms on a dose-for-dose basis.

Because of the limitations related to the low aqueous solubility of tadalafil, there is a need to develop novel forms that have improved physico-chemical properties including aqueous solubility, which can be formulated for use in oral administration to achieve faster onset or possibly improve its clinical profile.

It is possible to tackle these limitations by generating novel crystalline forms of tadalafil that includes crystalline molecular complexes, such as cocrystals, thereof that can improve the rate of dissolution, shorten Tmax, achieve rapid onset and reduce residence time in the GI tract.

SUMMARY OF THE INVENTION

The invention is directed towards generating novel compositions and crystalline forms of tadalafil that could improve aqueous solubility, rate of dissolution and/or shorten Tmax. One aspect of the present invention includes novel crystalline molecular complexes of tadalafil, such as cocrystals, and mixtures containing such materials. In addition, the invention further includes methods for the preparation of such complexes and compositions of crystalline molecular complexes of tadalafil suitable as an API (active pharmaceutical ingredient) in a pharmaceutical dosage form. Specific molecular complexes pertaining to the disclosure include, but are not limited to, complexes of tadalafil with oxalic acid, 4-hydroxybenzoic acid, malonic acid, 3-phenylpropanoic acid, methylparaben and propylparaben.

The foregoing and other features and advantages of the invention will become more apparent from the following detailed description, which proceeds with reference to the accompanying drawings. Such description is meant to be illustrative, and not limiting, of the invention. Obvious variants of the disclosed tadalafil forms in the text, including those described by the drawings and examples will be readily apparent to the person of ordinary skill in the art having the present disclosure, and such variants are considered to be a part of the current invention.

DETAILED DESCRIPTION OF THE INVENTION

The invention provides new crystalline molecular complexes, such as cocrystals, of tadalafil to improve its physicochemical characteristics and possible clinical profiles. For example, as discussed above, a new crystalline form is particularly advantageous if it can improve the aqueous solubility of tadalafil. Additionally, the crystal properties conferred upon the new crystal forms are also useful when the bioavailability is improved and its plasma concentration and/or serum concentration is improved which is particularly advantageous for orally delivered formulations.

A number of novel tadalafil crystalline forms have been synthesized, characterized, and disclosed herein. The novel tadalafil crystalline forms may be formulated in pharmaceutical dosage forms as known in the art for tadalafil and administered for the same therapeutic uses. The techniques and approaches set forth herein can further be used by the person of ordinary skill in the art to prepare obvious variants thereof, said variants considered to be part of the inventive disclosure.

Accordingly, in a first aspect, the invention relates to crystalline molecular complexes of tadalafil with a co-former. The co-former may be a short-chain short to medium chain organic acid, such as oxalic acid or malonic acid; a hydroxybenzoic acid or a hydroxybenzoic acid ester, such as 4-hydroxybenzoic acid, salicylic acid, methylparaben, a propylparaben (e.g. n-propylparaben, isopropylparaben); or a phenyl alkanoic acid, such as 3-phenylpropanoic acid. Other possible co-formers are described in U.S. Pat. No. 7,452,555 and U.S. Patent Application 2003/0224006 A1, which are incorporated here by reference. The molar ratio of the co-former in the molecular complex may range from 1:3 to 3:1 or preferably 1:2 to 2:1. The crystalline molecular complexes may be prepared using known techniques such as dry or solvent grinding, heating, slurrying or solvent evaporation of their solution in single or mixed solvent systems.

In one aspect, the invention relates to a 1:1 crystalline molecular complex of tadalafil with methylparaben. As shown in the examples below a 1:1 crystalline molecular complex of tadalafil and methylparaben may be prepared by dry grinding or in a solvent slurry. As tadalafil and methylparaben have been shown to cocrystallize, this crystalline molecular complex of the invention may also be prepared by other techniques known in the art such as, but not limited to, solvent grinding, heating, or solvent evaporation of their solution in single or mixed solvent systems.

Another aspect of the invention relates to a 1:1 crystalline molecular complex of tadalafil with propylparaben. As shown in the examples below a 1:1 crystalline molecular complex of tadalafil and propylparaben may be prepared by dry grinding or in a solvent slurry. As tadalafil and methylparaben have been shown to cocrystallize, this crystalline molecular complex of the invention may also be prepared by other techniques known in the art such as, but not limited to, solvent grinding, heating, or solvent evaporation of their solution in single or mixed solvent systems.

Another aspect of the invention relates to a 1:2 crystalline molecular complex of tadalafil with 4-hydroxybenzoic acid. As shown in the examples below a 1:2 crystalline molecular complex of tadalafil and 4-hydroxybenzoic acid may be prepared by dry grinding or in a solvent slurry. As tadalafil and 4-hydroxybenzoic acid have been shown to cocrystallize, this crystalline molecular complex of the invention may also be prepared by other techniques known in the art such as, but not limited to, solvent grinding, heating, or solvent evaporation of their solution in single or mixed solvent systems.

Another aspect of the invention relates to a 1:1 crystalline molecular complex of tadalafil with malonic acid. As shown in the examples below a 1:1 crystalline molecular complex of tadalafil and malonic acid may be prepared by dry grinding or in a solvent slurry. As tadalafil and malonic acid have been shown to cocrystallize, this crystalline molecular complex of the invention may also be prepared by other techniques known in the art such as, but not limited to, solvent grinding, heating, or solvent evaporation of their solution in single or mixed solvent systems.

Another aspect of the invention relates to a 1:1 crystalline molecular complex of tadalafil with oxalic acid. As shown in the examples below a 1:1 crystalline molecular complex of tadalafil and oxalic acid may be prepared by dry grinding. As tadalafil and oxalic acid have been shown to cocrystallize, this crystalline molecular complex of the invention may also be prepared by other techniques known in the art such as, but not limited to, solvent grinding, heating, a solvent slurry, or solvent evaporation of their solution in single or mixed solvent systems.

Another aspect of the invention relates to a 1:1 crystalline molecular complex of tadalafil with 3-phenylpropanoic acid. As shown in the examples below a 1:1 crystalline molecular complex of tadalafil and 3-phenylpropanoic acid may be prepared by dry grinding or in a solvent slurry. Another aspect of the invention provides a crystalline molecular complex of tadalafil and 3-phenylpropanoic acid by dissolving both compounds in acetonitrile and allowing the solvent mixtures to evaporate. As tadalafil and 3-phenylpropanoic acid have been shown to cocrystallize, this crystalline molecular complex of the invention may also be prepared by other techniques known in the art such as, but not limited to, solvent grinding, heating, or solvent evaporation of their solution in single or mixed solvent systems.

Another aspect of the invention provides crystalline molecular complexes of tadalafil as discussed above and, as particular examples, crystalline molecular complexes with 4-hydroxybenzoic acid, malonic acid, oxalic acid, 3-phenylpropanoic acid, methylparaben and propylparaben, suitable for pharmaceutical formulations than can be delivered via different routes to the human body. In addition to the crystalline molecular complex such pharmaceutical formulations may include one or more pharmaceutically acceptable carriers, including, without limitation, binders, fillers, lubricants, emulsifiers, suspending agents, sweeteners, flavorings, preservatives, buffers, wetting agents, disintegrants, effervescent agents and other conventional excipients and additives. The crystalline tadalafil molecular complexes of the invention and pharmaceutical formulations containing them may be used in the same therapies known for tadalafil itself. Pharmaceutical formulations of tadalafil, its therapeutic uses, and methods of treatment are described U.S. Pat. Nos. 5,859,006; 6,140,329; 6,821,975; 6,943,166; and 7,182,958 as mentioned above.

EXAMPLES

The following examples illustrate the invention without intending to limit its scope.

Preparative Examples

Tadalafil as a starting material used in all experiments in this disclosure was supplied by Beijing Apifocus Co. Ltd., China with stated chemical purity of 99.9%. Further purification through recrystallization from a solvent such as THF was needed to improve crystallinity and get rid of suspected physical impurities that could interfere with solid phase characterization.

Example 1

Preparation of Tadalafil and Oxalic Acid Complex (1:1)

120 mg of tadalafil was ground with 28 mg of oxalic acid and 20 µL of acetonitrile was added to the solid mixture. The solids gathered after grinding were stored in screw cap vials for subsequent analysis.

Example 2

Preparation of Tadalafil and 4-Hydroxybenzoic Acid Complex (1:2)

123.2 mg of tadalafil was ground with 88.3 mg of 4-hydroxybenzoic acid and 40 µL of acetonitrile was added to the solid mixture. The solids gathered after grinding were stored in screw cap vials for subsequent analysis.

Example 3

Preparation of Tadalafil and 4-Hydroxybenzoic Acid Complex (1:2) by Slurry Method 1000 mg of tadalafil was slurried with 710 mg of 4-hydroxybenzoic acid and 5 mL of acetonitrile. The solids gathered after the slurry were dried and stored in a screw cap vial for subsequent analysis.

Example 4

Preparation of Tadalafil and 3-Phenylpropanoic Acid Complex (1:1)

110 mg of tadalafil was ground with 42 mg of 3-phenylpropanoic acid and 20 µL of acetonitrile was added to the solid mixture. The solids gathered after grinding were stored in screw cap vials for subsequent analysis.

Example 5

Preparation of Tadalafil and 3-Phenylpropanoic Acid Complex (1:1) by Slurry Method 50 mg of tadalafil was slurried with 288.75 mg of 3-phenylpropanoic acid and 1 mL of acetonitrile. The solids gathered after the slurry were dried and stored in a screw cap vial for subsequent analysis.

Example 6

Preparation of Tadalafil and Malonic Acid Complex (1:1)

110 mg of tadalafil was ground with 30 mg of malonic acid and 40 µL of acetonitrile was added to the solid mixture. The solids gathered after grinding were stored in screw cap vials for subsequent analysis.

Example 7

Preparation of Tadalafil and Malonic Acid Complex (1:1) by Slurry Method 200 mg of tadalafil was slurried with 212 mg of malonic acid and 1 mL of acetonitrile. The solids gathered after the slurry were dried and stored in a screw cap vial for subsequent analysis.

Example 8

Preparation of Tadalafil and Methylparaben Complex (1:1)

100 mg of tadalafil was ground with 39 mg of methylparaben and 20 µL of acetonitrile was added to the solid mixture. The solids gathered after grinding were stored in screw cap vials for subsequent analysis.

Example 9

Preparation of Tadalafil and Methylparaben Complex (1:1) by Slurry method 200 mg of tadalafil was slurried with 156 mg of methylparaben and 1 mL of acetonitrile. The solids gathered after the slurry were dried and stored in a screw cap vial for subsequent analysis.

Example 10

Preparation of Tadalafil and Propylparaben Complex (1:1)

100 mg of tadalafil was ground with 46 mg of propylparaben and 20 µL of acetonitrile was added to the solid mixture. The solids gathered after grinding were stored in screw cap vials for subsequent analysis.

Example 11

Preparation of Tadalafil and Propylparaben Complex (1:1) by Slurry Method 200 mg of tadalafil was slurried with 184 mg of propylparaben and 1 mL of acetonitrile. The solids gathered after the slurry were dried and stored in a screw cap vial for subsequent analysis.

Characterization Examples

Analytical techniques used to observe the crystalline forms include Fourier Transform FTIR Spectroscopy (FTIR) and powder X-ray diffraction (PXRD). The particular methodology used in such analytical techniques should be viewed as illustrative, and not limiting in the context of data collection. For example, the particular instrumentation used to collect data may vary; routine operator error or calibration standards may vary; sample preparation method may vary (for example, the use of the KBr disk or Nujol mull technique for FTIR analysis).

Powder X-Ray Diffraction (PXRD): All cocrystal products were observed by a D-8 Bruker X-ray Powder Diffraction using Cu Kα ($\lambda$=1.540562 Å), 40 kV, 40 mA. The data was collected over an angular range of 3 to 40°2θ in continuous scan mode using a step size of 0.05°2θ and a scan speed of 1.0°/min. Peaks are reported at °2θ±0.2°2θ.

Fourier Transform FTIR Spectroscopy (FTIR): FTIR analysis was performed on a Perkin Elmer Spectrum 100 FTIR spectrometer equipped with a solid-state ATR accessory. Peaks are reported at $cm^{-1}$±1 $cm^{-1}$.

Example 12

Characterization of Tadalafil and Oxalic Acid Complex (1:1)

Figure 1:
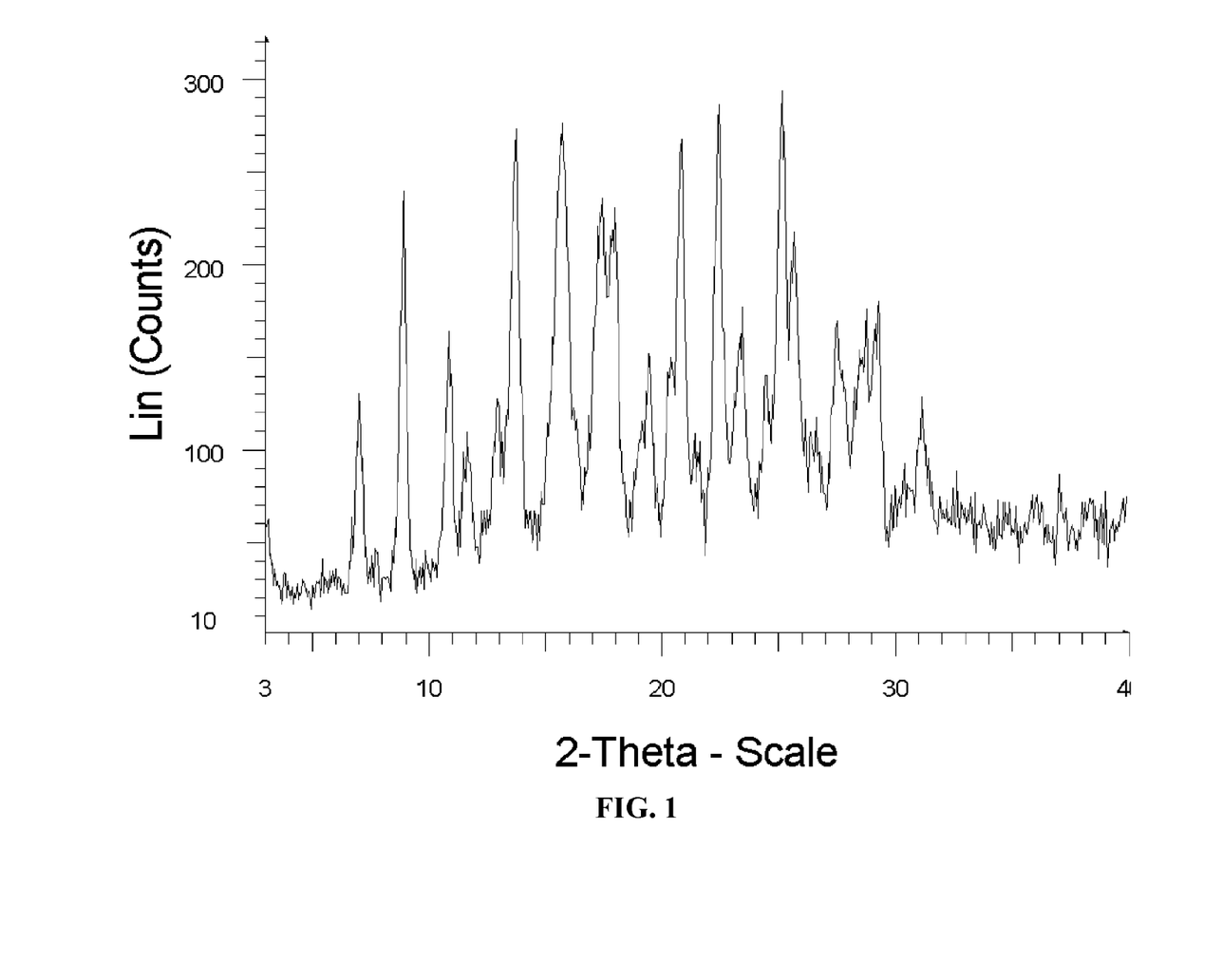
FIG. 1 shows a PXRD diffractogram of a crystalline tadalafil and oxalic acid molecular complex (1:1).

The PXRD diffractogram of a tadalafil and oxalic acid complex (1:1) is shown in FIG. 1. Table 1 below lists representative peaks from the PXRD pattern of FIG. 1. The representative peaks in Table 1 or a subset of those peaks, as well as the peaks shown in FIG. 1 or a subset of those peaks, can be used to characterize the tadalafil and oxalic acid crystalline molecular complex (1:1) of the invention.

Figure 2:
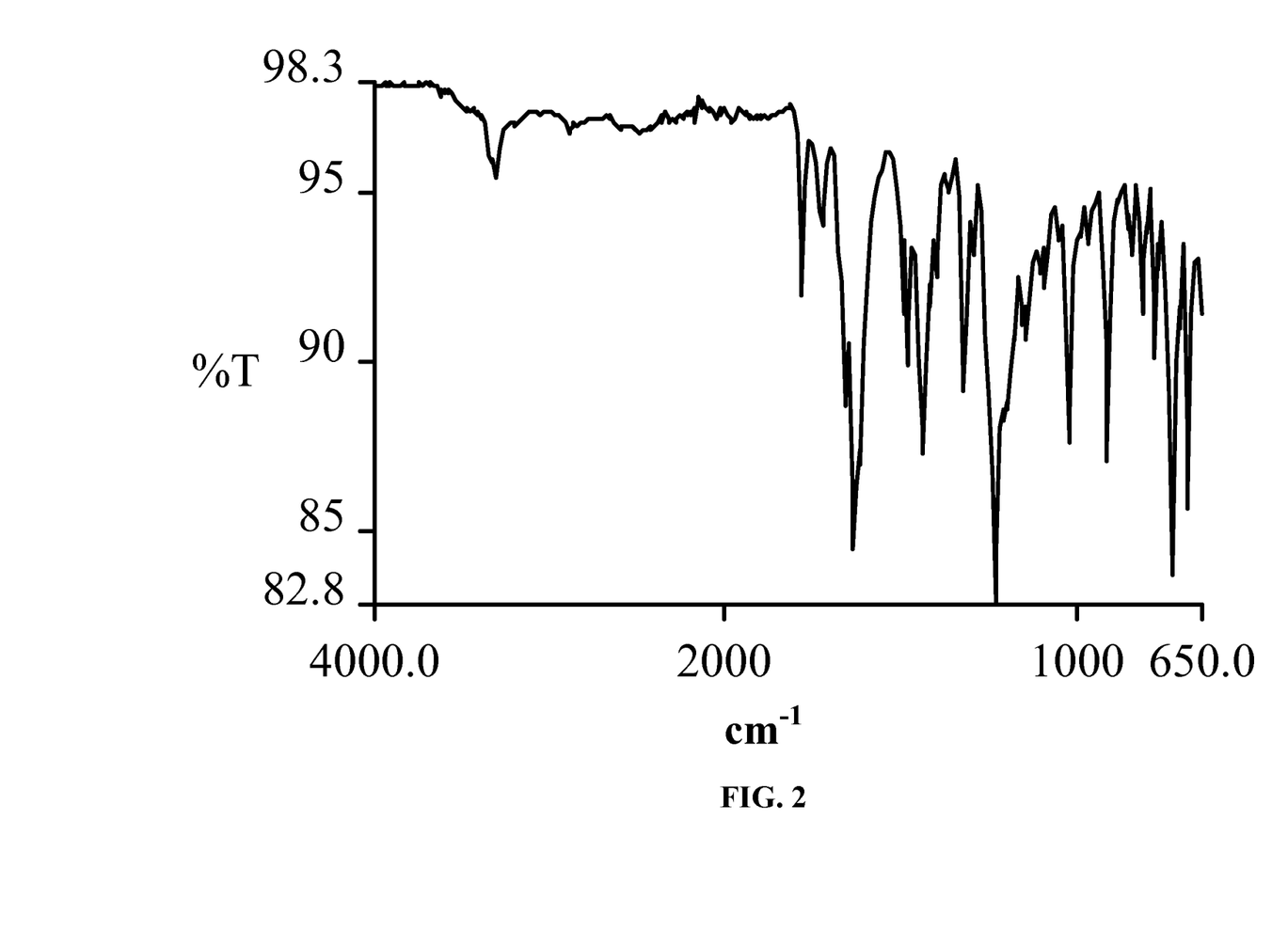
FIG. 2 shows an FTIR spectrum of a crystalline tadalafil and oxalic acid molecular complex (1:1).

FIG. 2 shows an FTIR spectrum of a tadalafil and oxalic acid complex (1:1). Table 2 below lists representative peaks from the FTIR spectrum of FIG. 2. The representative peaks in Table 2 or a subset of those peaks, as well as the peaks shown in FIG. 2 or a subset of those peaks, can be used to characterize the tadalafil and oxalic acid crystalline molecular complex (1:1) of the invention.

Example 13

Characterization of Tadalafil and 4-Hydroxybenzoic Acid Complex (1:2)

Figure 3:
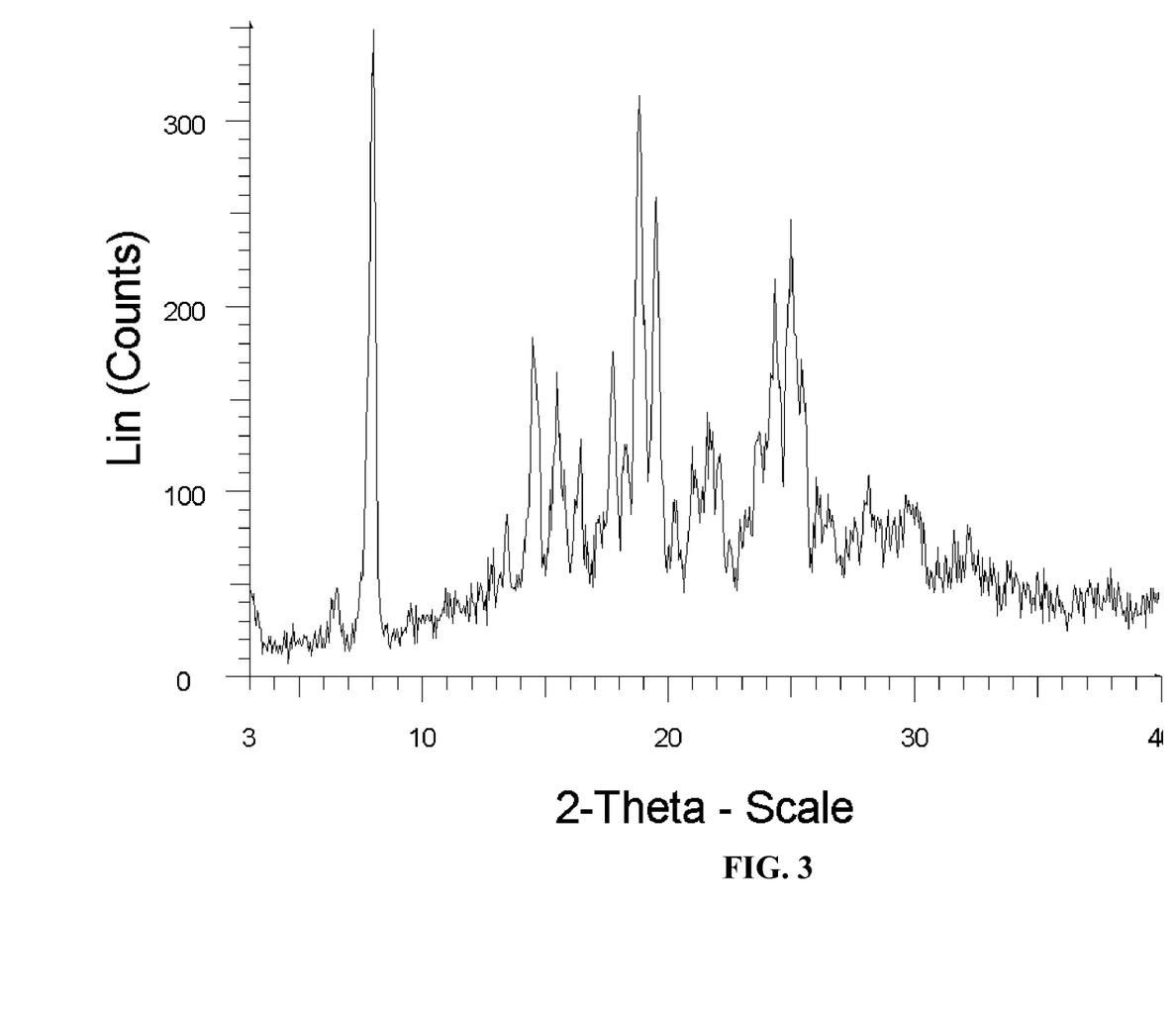
FIG. 3 shows a PXRD diffractogram of a crystalline tadalafil and 4-hydroxybenzoic acid molecular complex (1:2).

The PXRD diffractogram of a tadalafil and 4-hydroxybenzoic acid complex (1:2) is shown in FIG. 3. Table 1 below lists representative peaks from the PXRD pattern of FIG. 3. The representative peaks in Table 1 or a subset of those peaks, as well as the peaks shown in FIG. 3 or a subset of those peaks, can be used to characterize the tadalafil and 4-hydroxybenzoic acid crystalline molecular complex (1:2) of the invention.

Figure 4:
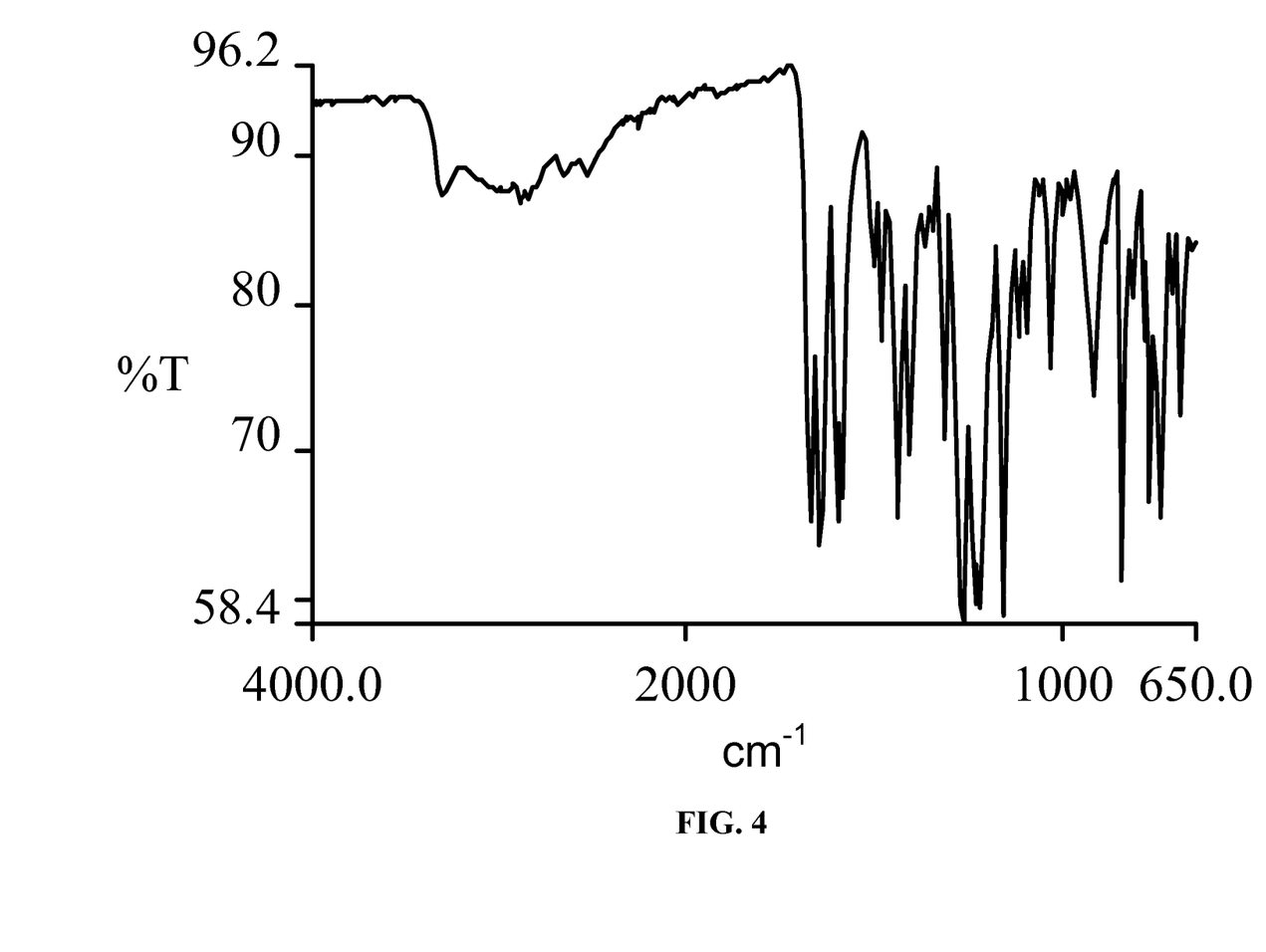
FIG. 4 shows an FTIR spectrum of a crystalline tadalafil and 4-hydroxybenzoic acid molecular complex (1:2).

FIG. 4 shows an FTIR spectrum of a tadalafil and 4-hydroxybenzoic acid complex (1:2). Table 2 below lists representative peaks from the FTIR spectrum of FIG. 4. The representative peaks in Table 2 or a subset of those peaks, as well as the peaks shown in FIG. 4 or a subset of those peaks, can be used to characterize the tadalafil and 4-hydroxybenzoic acid crystalline molecular complex (1:2) of the invention.

Example 14

Characterization of Tadalafil and 3-Phenylpropanoic Acid Complex (1:1)

Figure 5:
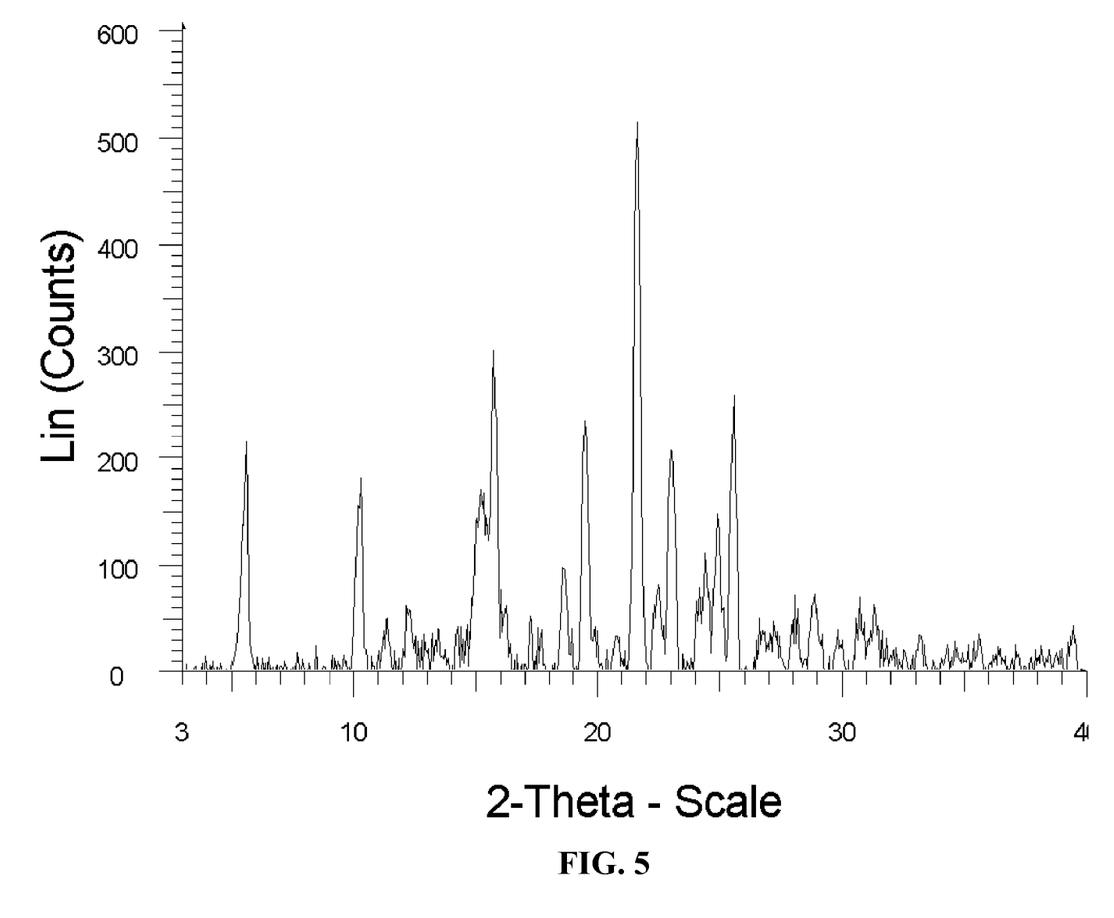
FIG. 5 shows a PXRD diffractogram of a crystalline tadalafil and 3-phenylpropanoic acid molecular complex (1:1).

The PXRD diffractogram of a tadalafil and 3-phenylpropanoic acid complex (1:1) is shown in FIG. 5. Table 1 below lists representative peaks from the PXRD pattern of FIG. 5. The representative peaks in Table 1 or a subset of those peaks, as well as the peaks shown in FIG. 5 or a subset of those peaks, can be used to characterize the tadalafil and 3-phenylpropanoic acid crystalline molecular complex (1:1) of the invention.

Figure 6:
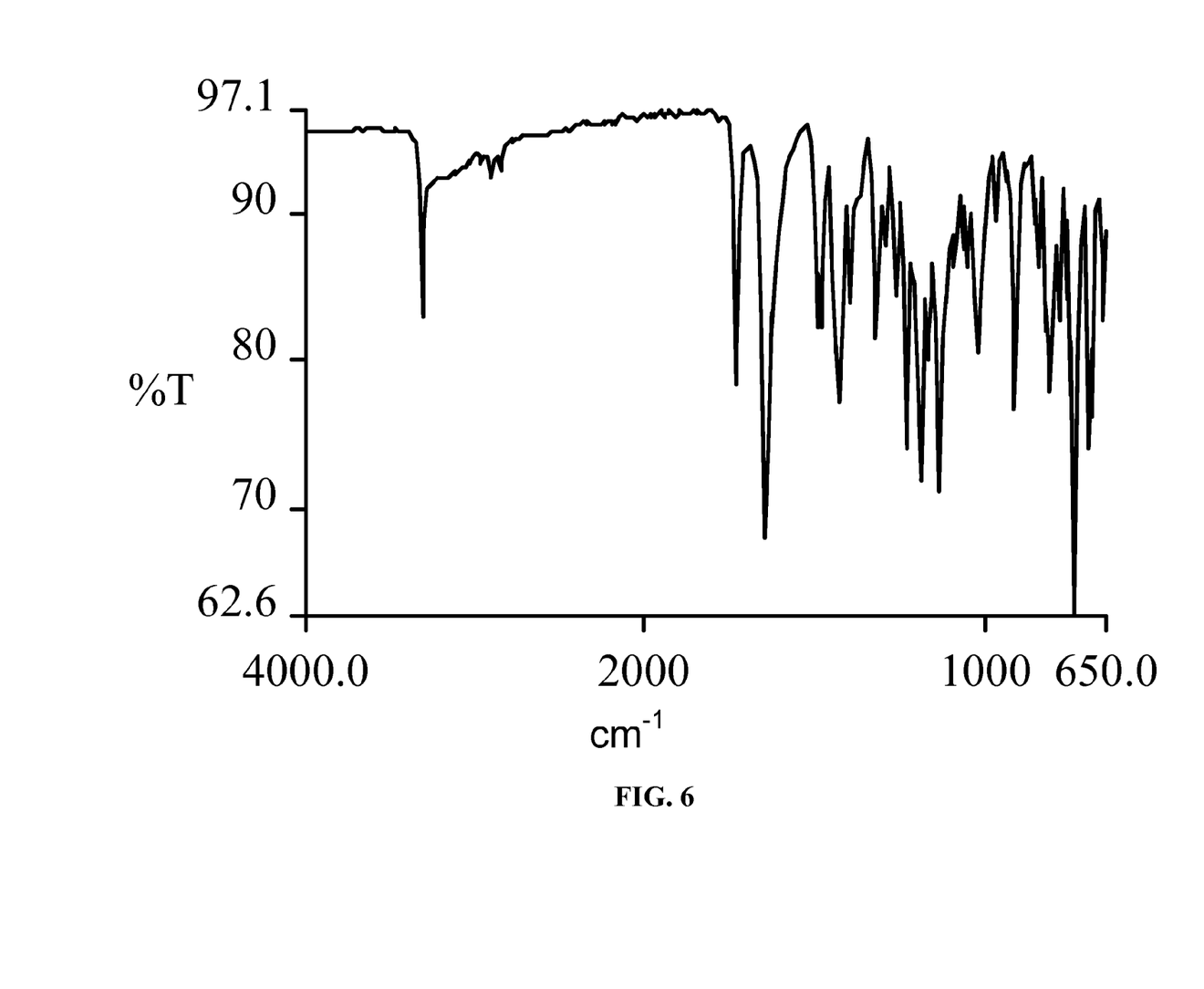
FIG. 6 shows an FTIR spectrum of a crystalline tadalafil and 3-phenylpropanoic acid molecular complex (1:1).

FIG. 6 shows an FTIR spectrum of a tadalafil and 3-phenylpropanoic acid complex (1:1). Table 2 below lists representative peaks from the FTIR spectrum of FIG. 6. The representative peaks in Table 2 or a subset of those peaks, as well as the peaks shown in FIG. 6 or a subset of those peaks, can be used to characterize the tadalafil and 3-phenylpropanoic acid crystalline molecular complex (1:1) of the invention.

Example 15

Characterization of Tadalafil and Malonic Acid Complex (1:1)

Figure 7:
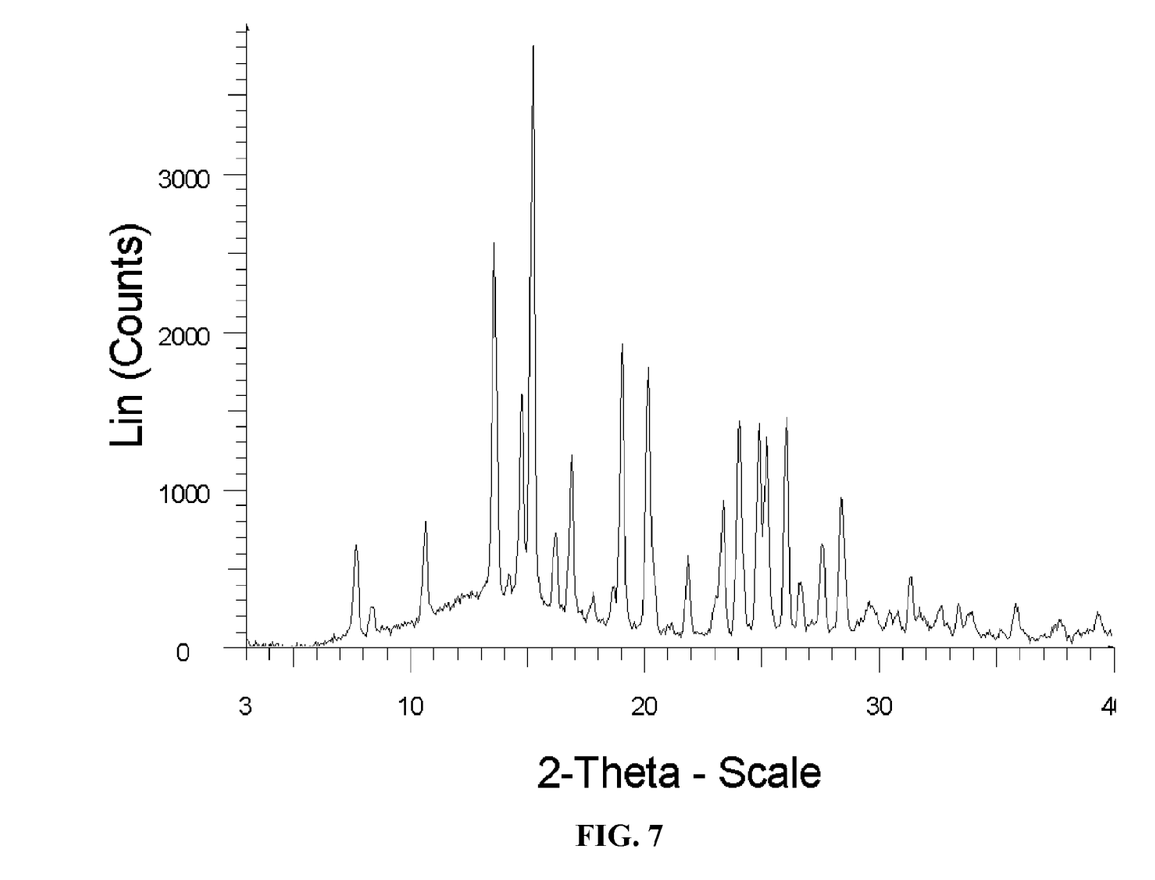
FIG. 7 shows a PXRD diffractogram of a crystalline tadalafil and malonic acid molecular complex (1:1).

The PXRD diffractogram of a tadalafil and malonic acid complex (1:1) is shown in FIG. 7. Table 1 below lists representative peaks from the PXRD pattern of FIG. 7. The representative peaks in Table 1 or a subset of those peaks, as well as the peaks shown in FIG. 7 or a subset of those peaks, can be used to characterize the tadalafil and malonic acid crystalline molecular complex (1:1) of the invention.

Figure 8:
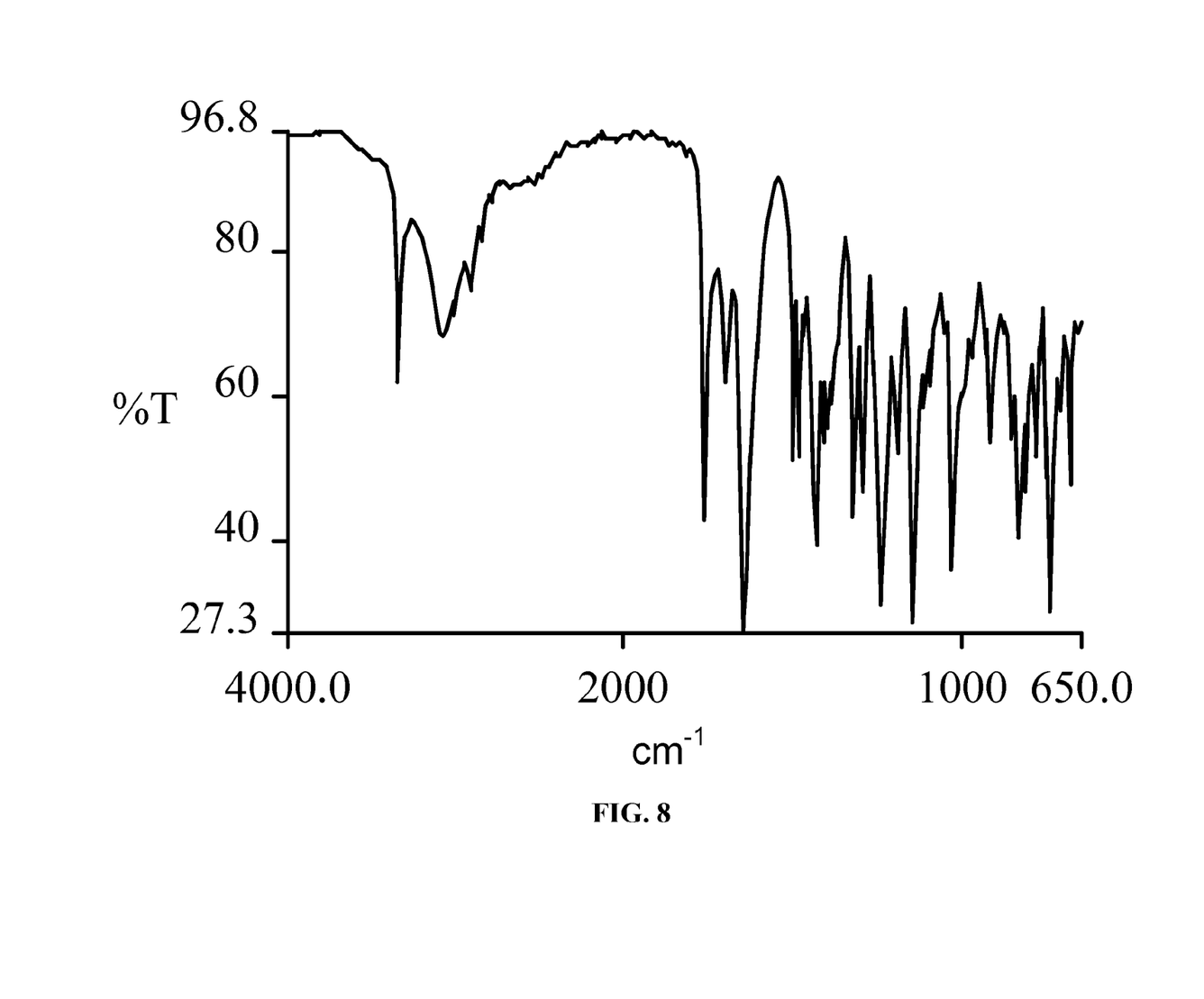
FIG. 8 shows an FTIR spectrum of a crystalline tadalafil and malonic acid molecular complex (1:1).

FIG. 8 shows an FTIR spectrum of a tadalafil and malonic acid complex (1:1). Table 2 below lists representative peaks from the FTIR spectrum of FIG. 8. The representative peaks in Table 2 or a subset of those peaks, as well as the peaks shown in FIG. 8 or a subset of those peaks, can be used to characterize the tadalafil and malonic acid crystalline molecular complex (1:1) of the invention.

Example 16

Characterization of Tadalafil and Methylparaben Complex (1:1)

Figure 9:
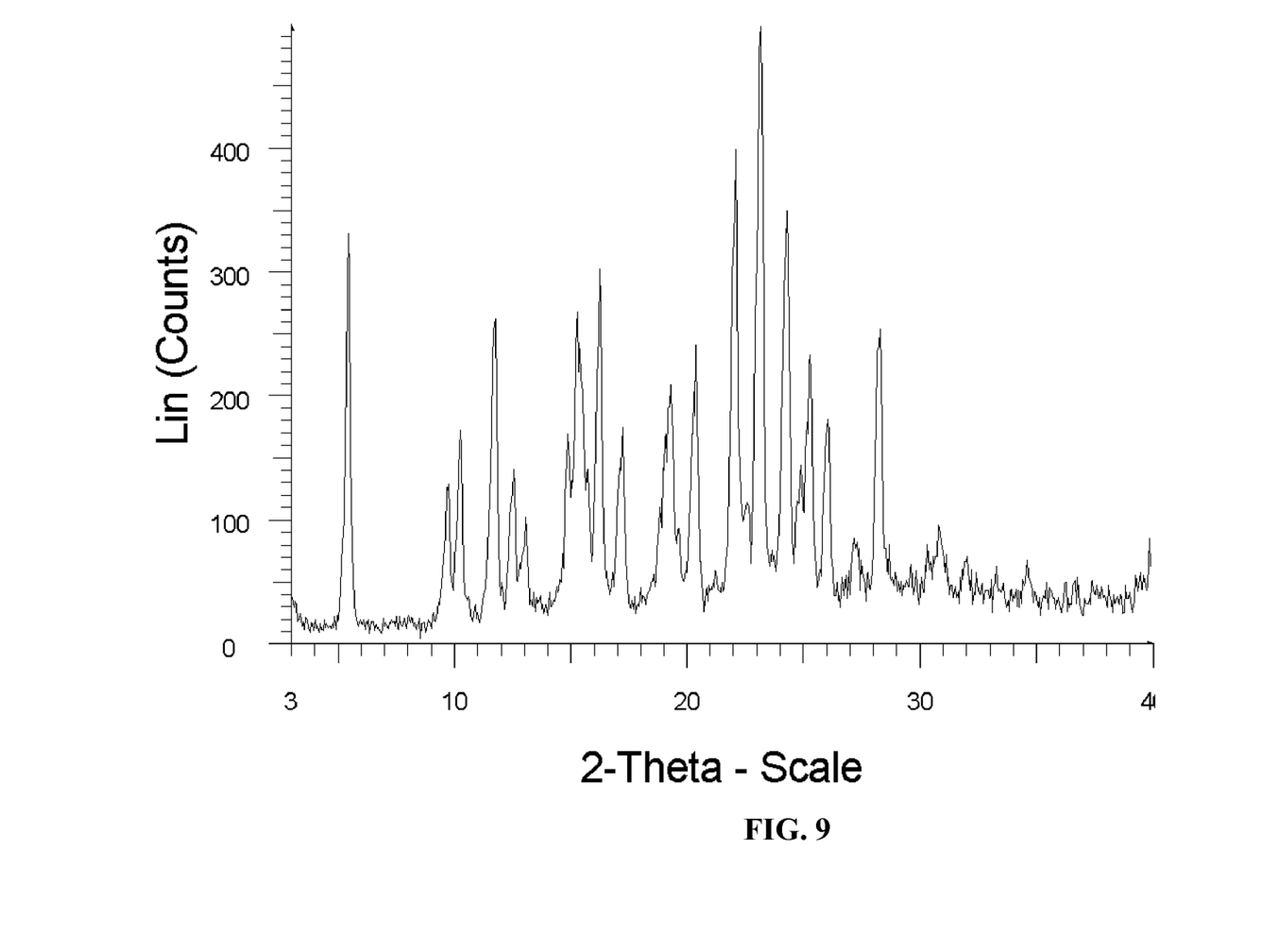
FIG. 9 shows a PXRD diffractogram of a crystalline tadalafil and methylparaben molecular complex (1:1).

The PXRD diffractogram of a tadalafil and methylparaben complex (1:1) is shown in FIG. 9. Table 1 below lists representative peaks from the PXRD pattern of FIG. 9. The representative peaks in Table 1 or a subset of those peaks, as well as the peaks shown in FIG. 9 or a subset of those peaks, can be used to characterize the tadalafil and methylparaben crystalline molecular complex (1:1) of the invention.

Figure 10:
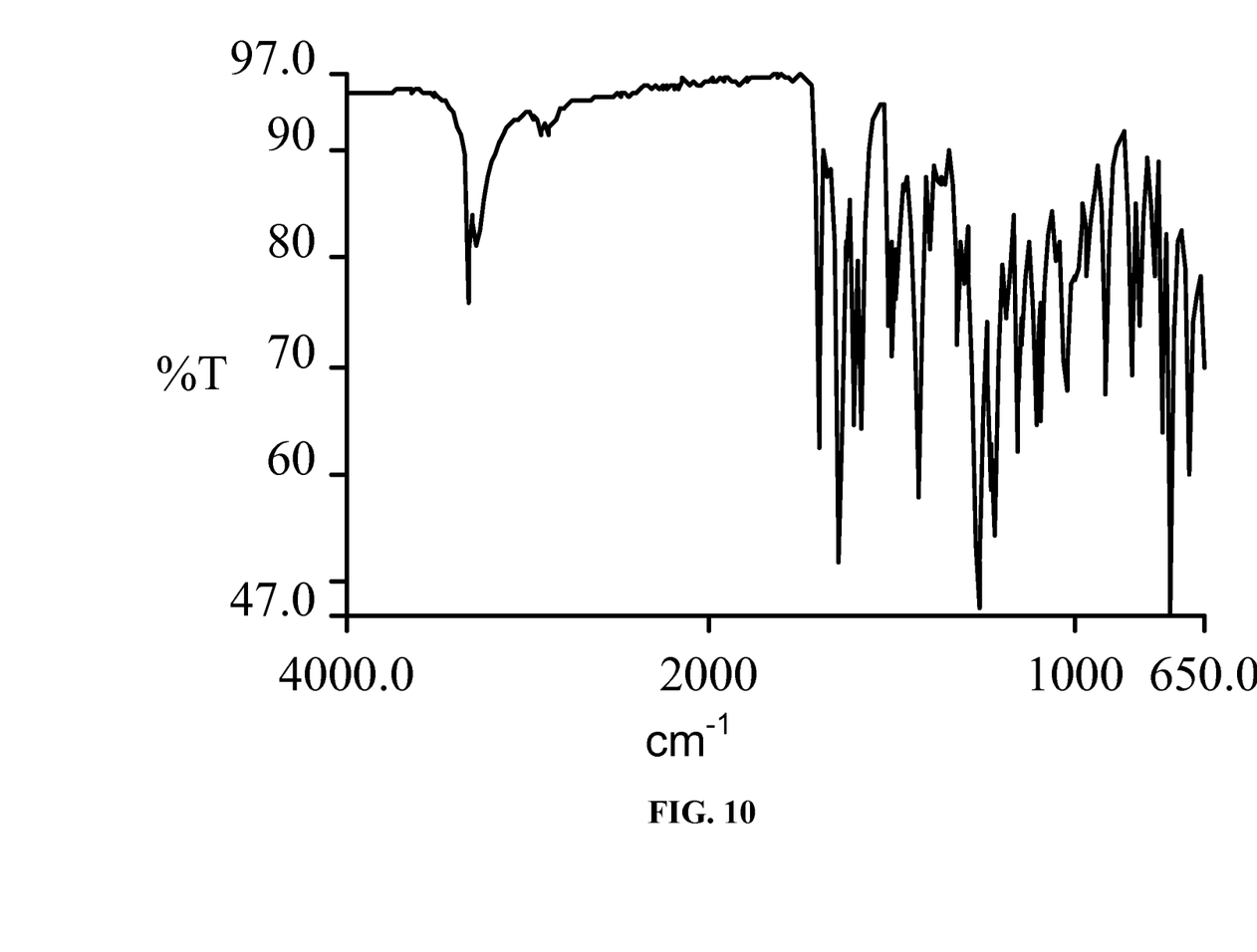
FIG. 10 shows an FTIR spectrum of a crystalline tadalafil and methylparaben molecular complex (1:1).

FIG. 10 shows an FTIR spectrum of a tadalafil and methylparaben complex (1:1). Table 2 below lists representative peaks from the FTIR spectrum of FIG. 10. The representative peaks in Table 2 or a subset of those peaks, as well as the peaks shown in FIG. 10 or a subset of those peaks, can be used to characterize the tadalafil and methylparaben crystalline molecular complex (1:1) of the invention.

Example 17

Characterization of Tadalafil and Propylparaben Complex (1:1)

Figure 11:
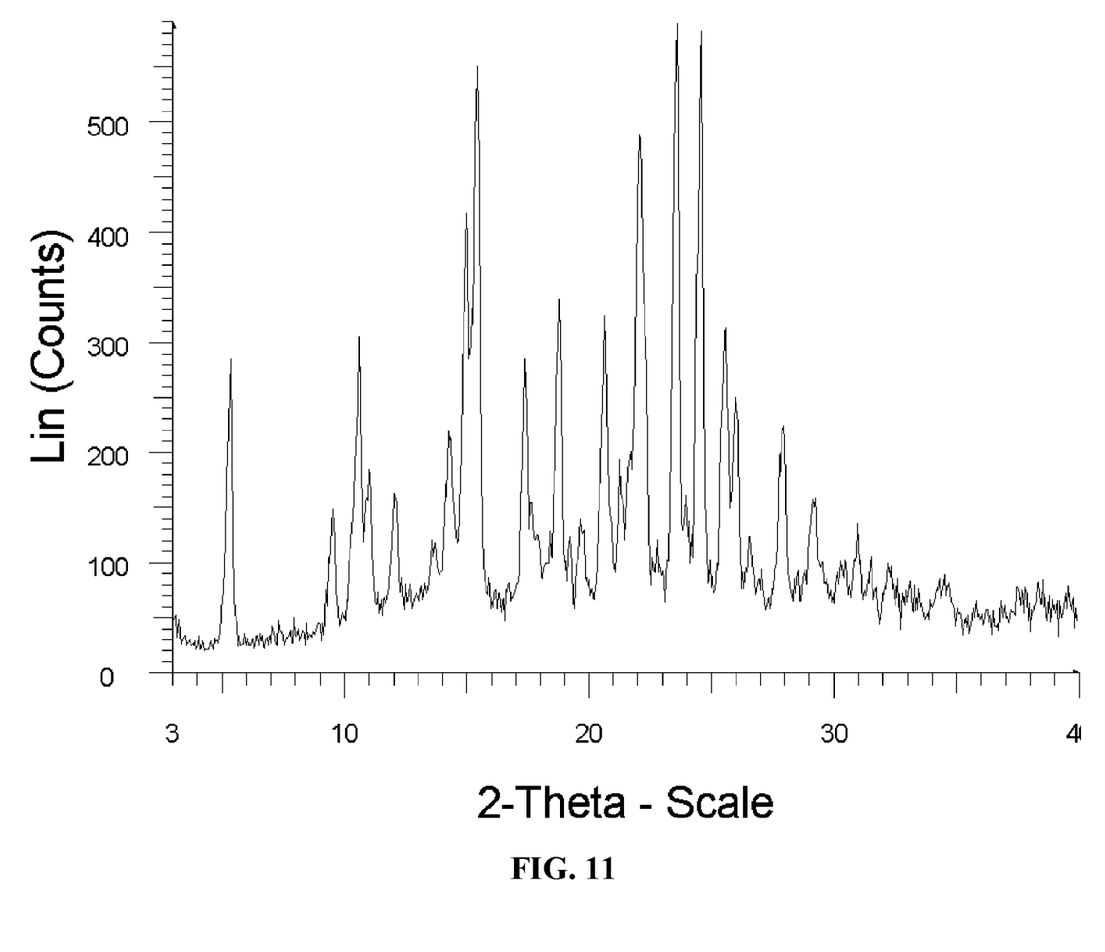
FIG. 11 shows a PXRD diffractogram of a crystalline tadalafil and propylparaben molecular complex (1:1).

The PXRD diffractogram of a tadalafil and propylparaben complex (1:1) is shown in FIG. 11. Table 1 below lists representative peaks from the PXRD pattern of FIG. 11. The representative peaks in Table 1 or a subset of those peaks, as well as the peaks shown in FIG. 11 or a subset of those peaks, can be used to characterize the tadalafil and propylparaben crystalline molecular complex (1:1) of the invention.

Figure 12:
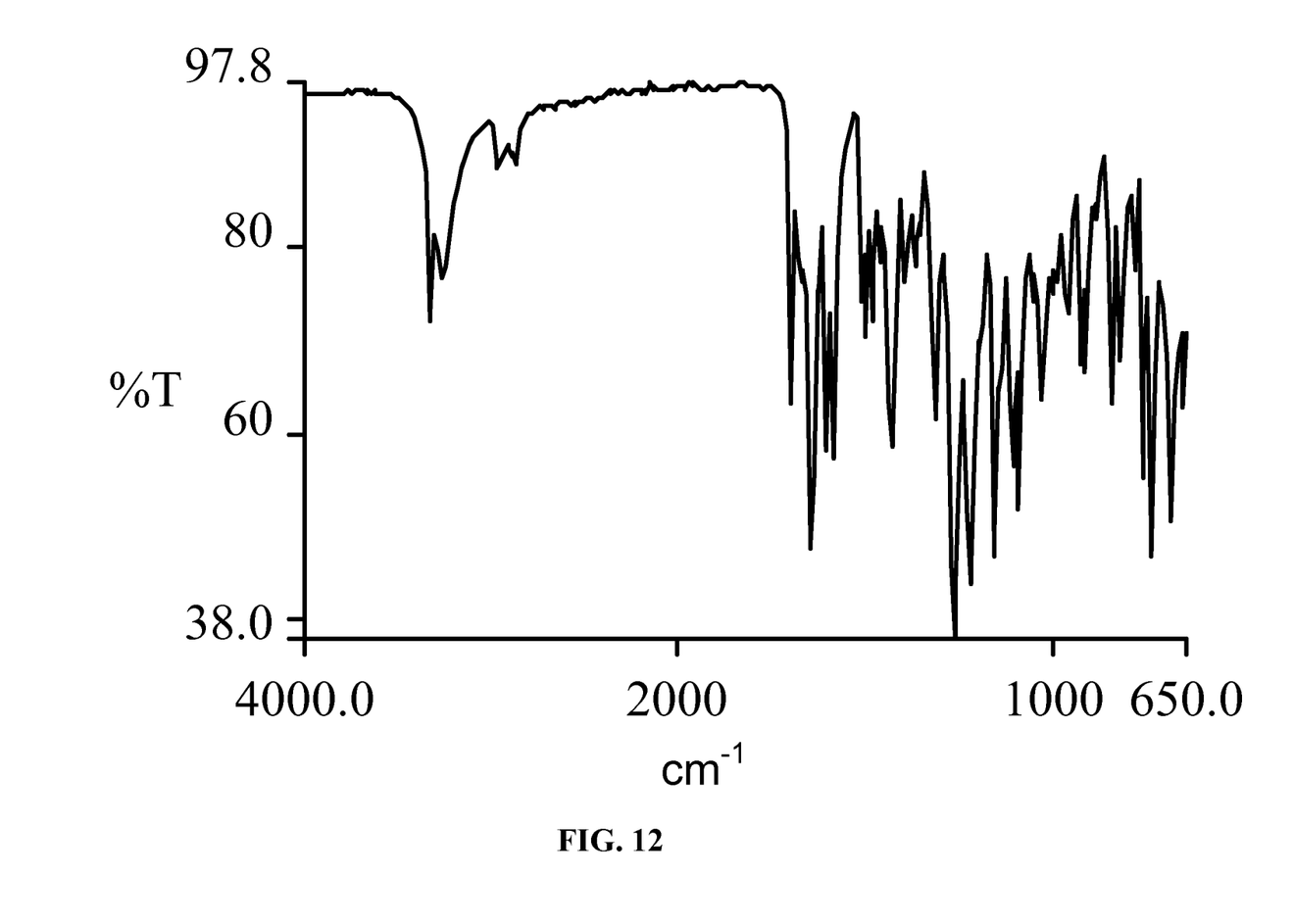
FIG. 12 shows an FTIR spectrum of a crystalline tadalafil and propylparaben molecular complex (1:1).

FIG. 12 shows an FTIR spectrum of a tadalafil and propylparaben complex (1:1). Table 2 below lists representative peaks from the FTIR spectrum of FIG. 12. The representative peaks in Table 2 or a subset of those peaks, as well as the peaks shown in FIG. 12 or a subset of those peaks, can be used to characterize the tadalafil and propylparaben crystalline molecular complex (1:1) of the invention.

TABLE 1

| PXRD Peaks, (°2θ ± 0.2 °2θ). | | | | | |
|---|---|---|---|---|---|
| Tadalafil: Oxalic Acid (1:1) | Tadalafil: 4-Hydroxybenzoic Acid (1:2) | Tadalafil: 3-Phenylpropanoic Acid (1:1) | Tadalafil: Malonic Acid (1:1) | Tadalafil: Methylparaben (1:1) | Tadalafil: Propylparaben (1:1) |
| 8.8 | 7.9 | 5.5 | 10.5 | 5.3 | 5.2 |
| 13.6 | 14.4 | 10.1 | 13.5 | 11.6 | 10.5 |
| 15.6 | 17.7 | 15.6 | 15.1 | 16.2 | 15.3 |
| 18.0 | 18.8 | 19.5 | 16.8 | 20.4 | 18.7 |
| 20.8 | 19.5 | 21.6 | 19.0 | 22.0 | 20.6 |
| 22.4 | 24.5 | 23.0 | 24.0 | 24.2 | 22.0 |
| 25.1 | 25.0 | 25.5 | 26.0 | 28.2 | 24.5 |

TABLE 2

| IR Peaks, (cm$^{-1}$ ± 1 cm$^{-1}$). | | | | | |
|---|---|---|---|---|---|
| Tadalafil: Oxalic Acid (1:1) | Tadalafil: 4-Hydroxybenzoic Acid (1:2) | Tadalafil: 3-Phenylpropanoic Acid (1:1) | Tadalafil: Malonic Acid (1:1) | Tadalafil: Methylparaben (1:1) | Tadalafil: Propylparaben (1:1) |
| 921 | 849 | 748 | 748 | 747 | 747 |
| 1032 | 921 | 919 | 1037 | 1225 | 1098 |
| 1241 | 1271 | 1143 | 1246 | 1266 | 1271 |
| 1441 | 1441 | 1432 | 1649 | 1432 | 1433 |
| 1637 | 1606 | 1645 | 1767 | 1646 | 1645 |
| 1784 | 1647 | 1737 | 3091 | 1706 | 1700 |
| 3316 | 1672 | 3324 | 3350 | 3343 | 3338 |

The claimed invention is:

1. A crystalline molecular complex of tadalafil comprising tadalafil and a co-former selected from methylparaben.

2. A crystalline molecular complex of tadalafil according to claim 1 where the molar ratio of the co-former in the complex ranges from 1:3 to 3:1.

3. A crystalline molecular complex of tadalafil according to claim 2 where the molar ratio of the co-former in the complex is from 1:1.

4. A crystalline molecular complex of tadalafil and methylparaben of claim 1, wherein the molecular complex is characterized by:
   an X-ray powder diffractogram having peaks at 5.3, 11.6, 16.2, 20.4, 22.0, 24.2, and 28.2°2θ±0.2°2θ;
   an infrared spectrum having peaks at 747, 1225, 1266, 1432, 1646, 1706, and 3343 cm$^{-1}$±1 cm$^{-1}$; or
   both.

5. A crystalline molecular complex of tadalafil and methylparaben of claim 1, wherein the molecular complex is characterized by at least one of the following:
   an X-ray powder diffractogram pattern substantially in accordance with the pattern shown in FIG. 9; or
   an FTIR spectrum substantially in accordance with the pattern shown in FIG. 10.

6. A pharmaceutical composition comprising a crystalline molecular complex of tadalafil and methylparaben of claim 4 and a pharmaceutically acceptable carrier.

7. A pharmaceutical composition comprising a crystalline molecular complex of tadalafil of claim 1 and a pharmaceutically acceptable carrier.

8. A method for making a crystalline molecular complex of tadalafil and methylparaben of claim 1, comprising the steps of:
   grinding tadalafil and methylparaben; and
   adding acetonitrile to the ground tadalafil and methylparaben.

9. A method for making a crystalline molecular complex of tadalafil and methylparaben of claim 1, comprising the steps of:
   slurrying tadalafil, methylparaben, and acetonitrile; and
   drying the slurried tadalafil, methylparaben, and acetonitrile.

* * * * *